United States Patent [19]
Thompson

[11] Patent Number: 5,541,304
[45] Date of Patent: Jul. 30, 1996

[54] CROSSLINKED HYDROGEL COMPOSITIONS WITH IMPROVED MECHANICAL PERFORMANCE

[75] Inventor: Samuel A. Thompson, Wilmington, Del.

[73] Assignee: Hercules Incorporated, Wilmington, Del.

[21] Appl. No.: 236,616

[22] Filed: May 2, 1994

[51] Int. Cl.$^6$ .................. C08L 5/08; A61M 25/00
[52] U.S. Cl. .................. 536/20; 524/916; 536/21; 536/102; 536/106; 536/114; 536/123.1; 536/123.12; 536/124; 623/1; 623/12; 623/900; 424/422; 424/423; 424/488
[58] Field of Search .................. 524/916; 536/20, 536/21, 102, 106, 114, 123.1, 123.12, 124; 514/54, 55, 56, 57, 60; 623/1, 12, 900; 424/422, 423, 488

[56] References Cited

U.S. PATENT DOCUMENTS

| | | | |
|---|---|---|---|
| 2,426,125 | 8/1947 | Steiner | 260/209.6 |
| 3,640,741 | 2/1972 | Estes | 106/170 |
| 4,042,770 | 8/1977 | Bachl et al. | 526/106 |
| 4,046,720 | 9/1977 | Rembaum et al. | 521/147 |
| 4,152,503 | 5/1979 | Short et al. | 526/106 |
| 4,183,884 | 1/1980 | Wichterle et al. | 264/41 |
| 4,476,243 | 10/1984 | Dombro | 502/236 |
| 4,547,571 | 10/1985 | Mukohyama et al. | 536/90 |
| 4,663,358 | 5/1987 | Hyon et al. | 521/64 |
| 4,734,097 | 3/1988 | Tanabe et al. | 623/11 |
| 4,774,957 | 10/1988 | Nambu et al. | 128/653.2 |
| 4,808,182 | 2/1989 | Barrett | 623/6 |
| 4,808,353 | 2/1989 | Nambu et al. | 264/28 |
| 4,822,361 | 4/1989 | Okita et al. | 623/12 |
| 4,870,966 | 10/1989 | Dellon et al. | 606/152 |
| 5,047,055 | 9/1991 | Bao et al. | 623/17 |
| 5,192,326 | 3/1993 | Bao et al. | 623/17 |
| 5,258,042 | 11/1993 | Mehta | 623/66 |

FOREIGN PATENT DOCUMENTS

| | | | |
|---|---|---|---|
| 0353896 | 2/1990 | European Pat. Off. | A61L 15/44 |

*Primary Examiner*—Gary L. Kunz
*Assistant Examiner*—Kathleen Kahler Fonda
*Attorney, Agent, or Firm*—Martin F. Sloan; Mark Goldberg

[57] ABSTRACT

This invention provides a method of altering the water content of a hydrogel comprising treatment of said hydrogel with a liquid dehydrating composition. There is further provided a method of altering the water content of a hydrogel-containing medical device. The medical devices of the present invention comprise a hydrogel having a water level ex vivo lower than the thermodynamic equilibrium water level when in vivo. These medical devices comprise a hydrogel contacted with a liquid dehydrating agent, wherein said medical device has a lower water level ex vivo than the thermodynamic equilibrium water level when the medical device is in vivo.

13 Claims, No Drawings

CROSSLINKED HYDROGEL COMPOSITIONS WITH IMPROVED MECHANICAL PERFORMANCE

This invention provides medical devices with improved mechanical performance and a method of producing these improved devices.

BACKGROUND OF THE INVENTION

Hydrogels offer excellent biocompatibility and have been shown to have reduced tendency for inducing thrombosis, encrustation and inflammation when used in medical devices. Unfortunately, the use of hydrogels in biomedical device applications has been hindered by poor mechanical performance. Many medical devices use hydrogels to improve device biocompatibility, however, the hydrogel can only be used in coatings as a result of insufficient mechanical performance for use as a bulk polymer. Hydrogels suffer from low modulus, low yield stress and low strength when compared to non-swollen polymer systems. Lower mechanical properties result from the swollen nature of hydrogels and the nonstress bearing nature of the swelling agent.

Polyols are well known plasticizers for polysaccharide dry films and are typically listed in the supplier literature as a preferred plasticizer. However, a plasticizer functions to lower modulus, lower yield stress, and often lowers strength.

U.S. Pat. No. 2,426,125 discloses the reaction between alginic acid in the form of threads, fibers or particles and certain lower epoxy paraffins or alkylene oxides to produce glycol alginates.

U.S. Pat. No. 3,640,741 discloses compositions which use polyols including glycerol as crosslinking agents for manufacture of slow dissolving plastic compositions. Excess polyol may be included as liquid media for carrying out the crosslinking reaction. Hydrophilic colloids such as carboxymethyl cellulose gum or alginate gum are crosslinked with the polyol to form a gel which exhibits slow dissolution in aqueous media. This reference does not disclose the formation of stable gels in the presence of water.

There remains the need to provide a means for temporarily reducing the swelling of hydrogel-containing medical devices to a controlled degree, thereby increasing modulus, yield stress and strength, while maintaining flexibility and the ability to return to the nascent hydrogel state once the device is placed in vivo. There also is the need for medical devices comprising hydrogels which can withstand aggressive physician handling without damage, sustain higher stresses encountered during implantation or insertion without inelastic deformation while retaining the original hydrogel properties in vivo.

SUMMARY OF THE INVENTION

This invention provides a method of controllably altering the water content of a hydrogel comprising treatment of said hydrogel with a liquid dehydrating composition. There is further provided a method of controllably altering the water content of a hydrogel-containing medical device. The medical devices of the present invention comprise a hydrogel having a controlled (or selected) water level ex vivo lower than the thermodynamic equilibrium water level when in vivo. These medical devices comprise a hydrogel contacted with a liquid dehydrating agent, wherein said medical device has a lower water level ex vivo than the thermodynamic equilibrium water level when the medical device is in vivo.

In another aspect of the present invention is provided a method of medical treatment with a medical device which comprises inserting into the body a hydrogel-containing medical device which has been treated with an agent which boosts mechanical performance of the medical device by displacing water from the hydrogel. The method of medical treatment of a human of the present invention comprises administering into the body a medical device, said medical device comprising a hydrogel which has been treated with an agent which increases mechanical performance of said medical device by reversibly displacing water from said medical device.

In another aspect of the present invention is provided a method of increasing mechanical performance of a hydrogel-containing medical device comprising treating said medical device with an agent which acts to reversibly dehydrate said hydrogel.

DETAILED DESCRIPTION OF THE INVENTION

The present invention provides a means for temporarily reducing the swelling of hydrogels to a controlled degree, thereby increasing modulus, yield stress and strength while maintaining flexibility and the ability to return to the nascent hydrogel state once the device is placed in vivo. A benefit of the invention is that medical devices comprising hydrogels treated with the dehydrating and swelling agents of this invention can better withstand aggressive physician handling without damage, sustain higher stresses encountered during implantation or insertion without inelastic deformation while retaining the original hydrogel properties upon rehydration in vivo. With respect to tubular medical devices this invention will facilitate increased resistance to columnar buckling forces experienced during insertion. The use of these agents also has the added benefit of providing for increased lubricity and resulting ease of insertion through small orifices and channels.

The present invention is applicable to all hydrogel materials. The term "hydrogel" is meant to be a water insoluble, water-containing material. Examples of hydrogels include synthetic polymers such as polyhydroxy ethyl methacrylate, and chemically or physically crosslinked polyvinyl alcohol, polyacrylamide, poly(N-vinyl pyrolidone), polyethylene oxide, and hydrolysed polyacrylonitrile. Examples of hydrogels which are organic polymers include covalent or ionically crosslinked polysaccharide-based hydrogels such as the polyvalent metal salts of alginate, pectin, carboxymethyl cellulose, heparin, hyaluronate and hydrogels from chitin, chitosan, pullulan, gellan and xanthan.

Conversion of a hydrogel to boost mechanical performance is effected by immersion in a new environment comprising at least one suitable agent such that the new environment acts to extract water from the gel and may also be accompanied by infiltration of the dehydrating agent such that the resultant improved device now contains less water and may contain some of the new environment. In the context of the present invention, the use of the term "reversibly displacing water" includes both complete reversibility wherein the gel rehydrates 100% as well as partial rehydration. In general, a dehydrating agent is any agent which can act to displace water from a hydrogel. Suitable agents include glycerol, glycols, alcohols, sugars and syrups. Among the specific agents which may be used include glycerol, ethylene glycol, poly(ethylene glycol), propane diols, butane diols, hexylene glycol, triethanol amine, corn syrup, high fructose corn syrup, mixtures of corn syrup and high fructose corn syrup, honey, alcohols, ketones and combinations thereof with water. Preferred agents for use in manufacturing the medical devices of the present invention include glycerol, poly(ethylene glycol), corn syrup, high fructose corn syrup, mixtures of corn syrup and high fructose corn syrup, and a mixture of 70/30 fructose in water. The most preferred agent is glycerol. The environment used to boost mechanical performance may be a single agent, a combination of active agents or agents in water. Once the medical device is introduced into the body, the dehydrating agent may become "fugitive" from the medical device and water may infiltrate the medical device.

EXAMPLE

Calcium-alginate fibers were prepared by spinning an aqueous solution of 7% sodium alginate into a 4% solution of $CaCl_2.2H_2O$ in water. One half of the fiber produced was placed into anhydrous glycerol for 2 hours. The fibers were tested to have the tensile strengths listed below in Table 1.

| Environment | Tensile Strength (psi) | Yield Strength (psi) |
| --- | --- | --- |
| Aqueous | 520 ± 30 | 48 ± 2 |
| Glycerol | 1390 ± 90 | 290 ± 30 |

What is claimed is:

1. A method of increasing the resistance to columnar buckling of a tubular hydrogel-containing medical device, said method comprising reversibly extracting water from said device by treatment of it with a liquid dehydrating composition to partially remove water therefrom to produce a tubular hydrogel-containing medical device with increased resistance to columnar buckling.

2. The method of claim 1 wherein said device comprises a member selected from the group consisting of polyhydroxy ethyl methacrylate, polyvinyl alcohol, polyacrylamide, poly(N-vinyl pyrolidone), polyethylene oxide, and hydrolyzed polyacrylonitrile.

3. The method of claim 1 wherein said device comprises polyvalent metal salts of at least one member selected from the group consisting of alginate, pectin, carboxymethyl cellulose, heparin, hyaluronate, pullulan, gellan and xanthan.

4. The method of claim 1 wherein said liquid dehydrating composition is selected from the group consisting of glycerol, ethylene glycol, poly(ethylene glycol), propane diols, butane diols, hexylene glycol, triethanol amine, corn syrup, high fructose corn syrup, mixtures of corn syrup and high fructose corn syrup, fructose, honey, alcohols, ketones and combinations thereof with water.

5. The method of claim 1 wherein said liquid dehydrating composition is selected from the group consisting of glycerol, poly(ethylene glycol), corn syrup, high fructose corn syrup, mixtures of corn syrup and high fructose corn syrup, fructose, and combinations thereof with water.

6. A tubular hydrogel-containing medical device immersed in a liquid dehydrating agent, wherein said device has a lower water level ex vivo than the thermodynamic equilibrium water level when in vivo, and wherein said medical device has increased resistance to columnar buckling.

7. The medical device of claim 6 wherein said device comprises a member selected from the group consisting of polyhydroxy ethyl methacrylate, polyvinyl alcohol, polyacrylamide, poly(N-vinylpyrolidone), polyethylene oxide, and hydrolysed polyacrylonitrile.

8. The medical device of claim 6 wherein said device comprises polyvalent metal salts of at least one member selected from the group consisting of alginate, pectin, carboxymethyl cellulose, heparin, hyaluronate, pullulan, gellan and xanthan.

9. The medical device of claim 6 wherein said dehydrating agent is selected from the group consisting of glycerol, ethylene glycol, poly(ethylene glycol), propane diols, butane diols, hexylene glycol, triethanol amine, corn syrup, high fructose corn syrup, mixtures of corn syrup and high fructose corn syrup, fructose, honey, alcohols, ketones and combinations thereof with water.

10. The medical device of claim 6 wherein said liquid dehydrating agent is selected from the group consisting of glycerol, poly(ethylene glycol), corn syrup, high fructose corn syrup, mixtures of corn syrup and high fructose corn syrup, fructose, and combinations thereof with water.

11. The medical device of claim 6 wherein said dehydrating agent is fugitive in vivo.

12. The method of claim 1 wherein said device comprises at least one polymer selected from the group consisting of chitin and chitosan.

13. The medical device of claim 6 wherein said device comprises at least one polymer selected from the group consisting of chitin and chitosan.

* * * * *